(12) United States Patent
Bae et al.

(10) Patent No.: US 11,064,949 B2
(45) Date of Patent: Jul. 20, 2021

(54) METHOD AND APPARATUS TO REMOVE NOISE FROM ELECTROCARDIOGRAPHY (ECG) SENSOR SIGNAL

(71) Applicant: Samsung Electronics Co., Ltd., Suwon-si (KR)

(72) Inventors: Chisung Bae, Yongin-si (KR); Jinhyun Yun, Seoul (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 305 days.

(21) Appl. No.: 15/485,295

(22) Filed: Apr. 12, 2017

(65) Prior Publication Data

US 2017/0340288 A1    Nov. 30, 2017

(30) Foreign Application Priority Data

May 26, 2016    (KR) ........................ 10-2016-0064725

(51) Int. Cl.
*A61B 5/00*    (2006.01)
*A61B 5/25*    (2021.01)
(Continued)

(52) U.S. Cl.
CPC ............ *A61B 5/7203* (2013.01); *A61B 5/117* (2013.01); *A61B 5/25* (2021.01); *A61B 5/316* (2021.01); *A61B 5/6898* (2013.01); *A61B 5/7264* (2013.01)

(58) Field of Classification Search
CPC ... A61B 5/0022; A61B 5/0245; A61B 5/0402; A61B 5/681; A61B 5/0006; A61B 5/04012; A61B 2018/00839; A61B 5/0468; A61B 5/7264; A61B 5/7203; A61B 5/7275; A61B 5/7221; A61B 5/7225; A61B 5/7246; A61B 5/02427; A61B 5/04017; A61B 5/04; A61B 5/0432; A61B 5/117; G06F 19/00; G06F 1/163; G06F 17/18; G06F 19/321; G06F 19/3418;
(Continued)

(56) References Cited

U.S. PATENT DOCUMENTS 3,858,034 A * 12/1974 Anderson .......... A61B 5/04017
                                                600/516
5,660,184 A    8/1997 Donehoo et al.
(Continued)

FOREIGN PATENT DOCUMENTS

JP    5-31087 A    2/1993
JP    6-277189 A   10/1994
(Continued)

*Primary Examiner* — Deborah L Malamud
(74) *Attorney, Agent, or Firm* — NSIP Law

(57) ABSTRACT

A method and an apparatus to remove a noise from an electrocardiography (ECG) sensor signal are provided. A noise removing method includes: receiving a sensor signal collected by an electrocardiography (ECG) sensor; extracting an ECG estimation signal from the sensor signal based on a peak value of the sensor signal; determining a first comparison value between the ECG estimation signal and a first reference signal indicating an average form of ECG signals; and classifying the ECG estimation signal as one of an ECG signal and a noise by comparing the first comparison value to a first threshold value.

18 Claims, 11 Drawing Sheets

(51) Int. Cl.
*A61B 5/316* (2021.01)
*A61B 5/117* (2016.01)

(58) Field of Classification Search
CPC ........ G16H 50/20; G16H 15/00; G16H 50/70; A61N 1/3702; A61N 1/3925; A61N 1/08; G06K 2009/00939; G06K 2209/05; G06K 9/00523; G06K 9/0053; G06K 9/00536
See application file for complete search history.

(56) References Cited

U.S. PATENT DOCUMENTS

| | | | |
|---|---|---|---|
| 5,908,393 | A | 6/1999 | Albrecht et al. |
| 8,428,700 | B2 * | 4/2013 | Harlev .................. G16H 10/60 |
| | | | 600/509 |
| 2003/0114768 | A1 | 6/2003 | Fischer |
| 2004/0049120 | A1 | 3/2004 | Cao et al. |
| 2007/0078324 | A1 | 4/2007 | Wijisiriwardana |
| 2010/0022903 | A1 | 1/2010 | Sitzman et al. |
| 2012/0016249 | A1 | 1/2012 | Lian et al. |
| 2012/0123232 | A1 * | 5/2012 | Najarian .............. A61B 5/0022 |
| | | | 600/345 |
| 2012/0245439 | A1 * | 9/2012 | Andre .................... A61B 5/412 |
| | | | 600/310 |
| 2012/0323132 | A1 | 12/2012 | Warner et al. |
| 2013/0190638 | A1 | 7/2013 | Chon et al. |
| 2014/0088399 | A1 * | 3/2014 | Lian ..................... A61B 5/0404 |
| | | | 600/393 |
| 2014/0136585 | A1 | 5/2014 | Brockway |
| 2014/0361871 | A1 | 12/2014 | Silva et al. |
| 2015/0018702 | A1 | 1/2015 | Galloway et al. |

FOREIGN PATENT DOCUMENTS

| | | |
|---|---|---|
| JP | 7-67844 A | 3/1995 |
| JP | 11-504541 A | 2/1999 |
| JP | 2002-521079 A | 7/2002 |
| JP | 2005-537888 A | 12/2005 |
| JP | 2011-72542 A | 4/2011 |
| JP | 2012-511954 A | 5/2012 |
| JP | 2012-210235 A | 11/2012 |
| JP | 2012-210236 A | 11/2012 |
| JP | 2013-150857 A | 8/2013 |
| KR | 1998-0000363 A1 | 3/1998 |
| KR | 10-0408498 B1 | 4/2004 |
| KR | 10-0750662 B1 | 8/2007 |
| KR | 10-1002020 B1 | 12/2010 |
| KR | 10-1235215 B1 | 2/2013 |
| KR | 10-2013-0140439 A | 12/2013 |
| KR | 10-1366101 B1 | 2/2014 |

* cited by examiner ic # METHOD AND APPARATUS TO REMOVE NOISE FROM ELECTROCARDIOGRAPHY (ECG) SENSOR SIGNAL

CROSS-REFERENCE TO RELATED APPLICATIONS

This application claims the benefit under 35 USC § 119(a) of Korean Patent Application No. 10-2016-0064725 filed on May 26, 2016, in the Korean Intellectual Property Office, the entire disclosure of which is incorporated herein by reference for all purposes.

BACKGROUND

1. Field

The following description relates to a method and an apparatus for removing a noise from an electrocardiography (ECG) sensor signal.

2. Description of Related Art

Due to developments in sensor technology, an individual may measure an electrocardiography (ECG) signal using a terminal. An ECG signal may be measured by an ECG sensor to be used for user authentication. When an ECG sensor measures an ECG signal, the ECG sensor may additionally pick up operating noise from a device or contact noise. Such noises may decrease reliability of the measured signal or delay linkage operations, such as user authentication.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a noise removing method includes: receiving a sensor signal collected by an electrocardiography (ECG) sensor; extracting an ECG estimation signal from the sensor signal based on a peak value of the sensor signal; determining a first comparison value between the ECG estimation signal and a first reference signal indicating an average form of ECG signals; and classifying the ECG estimation signal as one of an ECG signal and a noise by comparing the first comparison value to a first threshold value.

The first reference signal may be generated based on an average of the ECG signals collected from at least one user.

The method may further include: determining a second comparison value between the ECG estimation signal and a second reference signal indicating an average form of contact noise signals.

The first comparison value and the second comparison value may be determined based on one of a cosine distance and a Euclidean distance. The classifying may include classifying the ECG estimation signal as the ECG signal, in response to the first comparison value being less than the first threshold value and the second comparison value being greater than a second threshold value.

The first comparison value may be determined based on one of a cosine distance between the ECG estimation signal and the first reference signal, a correlation between the ECG estimation signal and the first reference signal, and a Euclidean distance between the ECG estimation signal and the first reference signal.

The first threshold value may be experimentally determined to remove the noise from the ECG estimation signal and classify users based on ECG.

The method may further include performing user authentication based on the ECG signal.

The determining may include: generating an inverted signal of the ECG estimation signal based on a sign of the first comparison value; and determining a comparison value between the inverted signal and the first reference signal as the first comparison value.

The method may further include: accumulating the ECG signals; and adjusting the first threshold value based on a distribution of the accumulated ECG signals.

The ECG sensor may be configured to collect the sensor signal through a dry type electrode.

The ECG sensor may include: a first electrode disposed in a bezel of a portable device and configured to collect the sensor signal from a hand of the user in contact with the first electrode; and a second electrode disposed in a home button of the portable device and configured to collect the sensor signal from another hand of the user in contact with the second electrode.

A non-transitory computer-readable storage medium may store instructions that, when executed by a processor, cause the processor to perform the method.

In another general aspect, a noise removing apparatus includes: an extractor configured to receive a sensor signal collected by an electrocardiography (ECG) sensor, and extract an ECG estimation signal from the sensor signal based on a peak value of the sensor signal; and a comparer configured to determine a first comparison value between the ECG estimation signal and a first reference signal indicating an average form of ECG signals, and classify the ECG estimation signal as one of an ECG signal and a noise by comparing the first comparison value to a first threshold value.

The first reference signal may be generated based on an average of the ECG signals collected from at least one user.

The comparer may be configured to determine a second comparison value between the ECG estimation signal and a second reference signal indicating an average form of contact noise signals.

The first comparison value and the second comparison value may be determined based on a cosine distance or a Euclidean distance. The comparer may be configured to classify the ECG estimation signal as the ECG signal, in response to the first comparison value being less than the first threshold value and the second comparison value being greater than a second threshold value.

The ECG signal may be used to perform user authentication.

In another general aspect, a noise removing method includes: collecting a sensor signal associated with electrocardiography (ECG) of a user using an ECG sensor; extracting an ECG estimation signal from the sensor signal based on a peak value of the sensor signal; determining a first comparison value between the ECG estimation signal and a first reference signal indicating an average form of ECG signals; determining a second comparison value between the ECG estimation signal and a second reference signal indicating an average form of contact noise signals, in response to the first comparison value being greater than a first threshold value; classifying the ECG estimation signal as an ECG signal, in response to the second comparison value being less than the second reference signal; and performing user authentication based on the ECG signal.

The method may further include: classifying the ECG estimation signal as a noise, in response to the first comparison value being greater than the first threshold value, wherein the first comparison value and the second comparison value are determined based on one of a cosine distance and a Euclidean distance.

The method may further include: classifying the ECG estimation signal as a noise, in response to the second comparison value being less than a second threshold value, wherein the first comparison value and the second comparison value are determined based on a cosine distance or a Euclidean distance.

The first reference signal may be generated based on an average of the ECG signals collected from at least one user.

A non-transitory computer-readable storage medium may store instructions that, when executed by a processor, cause the processor to perform the method.

Other features and aspects will be apparent from the following detailed description, the drawings, and the claims.

Figure 1:
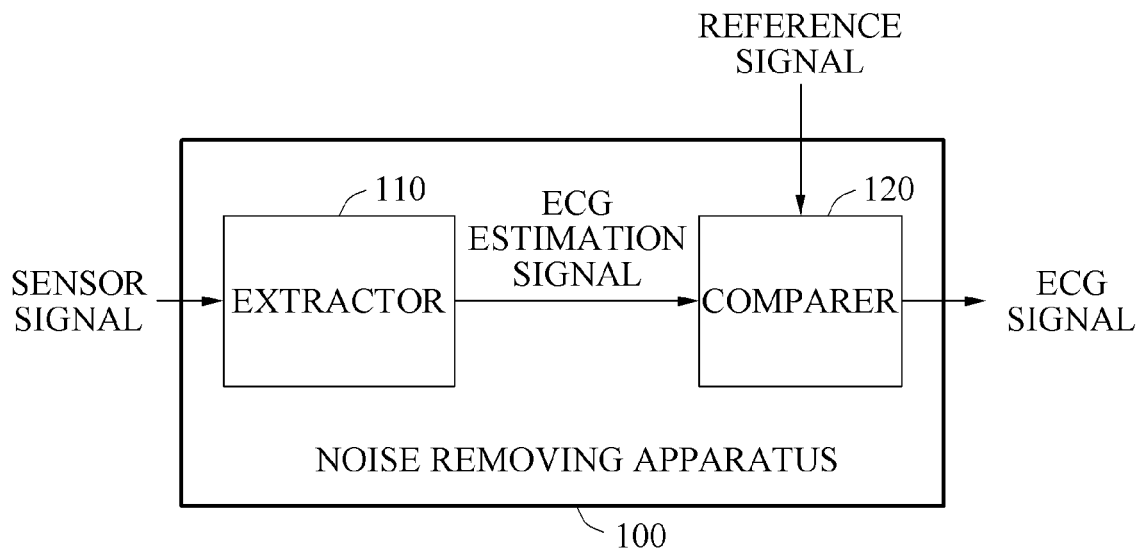
FIG. 1 is a block diagram illustrating an example of a noise removing apparatus configured to output an electrocardiography (ECG) signal based on a sensor signal.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

FIG. 1 is a block diagram illustrating an example of a noise removing apparatus 100 configured to output an electrocardiography (ECG) signal based on a sensor signal. Referring to FIG. 1, the noise removing apparatus 100 includes an extractor 110 and a comparer 120. The extractor 110 receives a sensor signal collected by an ECG sensor and extracts an ECG estimation signal from the sensor signal based on a peak value of the sensor signal. The ECG estimation signal is a signal estimated to be an ECG signal. The ECG estimation signal may be classified as a noise or an ECG signal by the comparer 120. Hereinafter, the ECG signal does not correspond to a noise signal among sensor signals. The ECG signal refers to a selected signal indicating an ECG of a user with a high reliability. The comparer 120 determines a comparison value between the ECG estimation signal and a reference signal, and classifies the ECG estimation signal as an ECG signal or a noise by comparing the determined comparison value to a threshold value. The comparer 120 outputs the ECG signal. The reference signal may be experimentally determined in advance and provided to the comparer 120.

The ECG signal output by the noise removing apparatus 100 is used to perform user authentication. For example, the ECG signal is used to unlock a portable device or to make a payment through an electronic commerce system. Since ECG signals differ from user to user, users may be identified based on the ECG signals. As accuracy of the ECG signal for user authentication increases, reliability of ECG signal based user authentication may increase. The accuracy of the ECG signal may increase as accuracy in classifying the ECG signal and a noise from the sensor signal collected by the ECG sensor increases. The ECG signal output by the noise removing apparatus 100 may be used for user health management. For example, the ECG signal is used to manage arrhythmia or a heart disease. As the accuracy of the ECG signal used to measure a health condition of the user increases, the health condition of the user may be more accurately measured.

The noise removing apparatus 100 accurately selects, using the reference signal, the ECG signal from the sensor signal. The reference signal includes a first reference signal indicating an average form of ECG signals and a second reference signal indicating an average form of contact noise signals. The first reference signal and the second reference signal may be experimentally determined. A noise includes a motion noise occurring due to vibration of a device and a contact noise occurring when the device is in contact with a body of a user. The motion noise may have an irregular form. Thus, the motion noise may be removed based on a similarity between the motion noise and the first reference signal indicating the average form of the ECG signals. The contact noise may have a form similar to a form of the first reference signal, in which case the contact noise may not be removed based on the similarity between the contact noise and the first reference signal. The contact noise may be removed based on the similarity between the contact noise and the second reference signal indicating the average form of the contact noise signals. Accordingly, the accuracy of the ECG signal may be increased using at least one of the first reference signal and the second reference signal and, as a result, the user authentication based on the ECG signal may be more accurate. The comparer 120 determines first comparison value, which is a comparison value between the ECG estimation signal and the first reference signal. The comparer 120 also determines a second comparison value, which is a comparison value between the ECG estimation signal and the second reference signal. A comparison value, such as the first comparison value or the second comparison value, may be a cosine distance, a correlation, or a Euclidean distance between the ECG estimation signal and the reference signal. In detail, the first comparison value is determined based on a cosine distance, a correlation, or a Euclidean distance between the ECG estimation signal and the first reference signal. Also, the second comparison value is determined based on a cosine distance, a correlation, or a Euclidean distance between the ECG estimation signal and the second reference signal.

When the comparison value is determined based on the cosine distance or the Euclidean distance, the ECG estimation signal may be different from the reference signal in response to the comparison value being increased. The comparer 120 classifies the ECG estimation signal as the ECG signal in response to the first comparison value being less than a predetermined or desired first threshold value, or the second comparison value being greater than a predetermined or desired second threshold value. Also, the comparer 120 classifies the ECG estimation signal as a noise in response to the first comparison value being greater than the predetermined first threshold value, or the second comparison value being less than the predetermined second threshold value. When the comparison value is determined based on the correlation, the comparer 120 classifies the ECG estimation signal as the ECG signal in response to the first comparison value being greater than the predetermined first threshold value or the second comparison value being less than the predetermined second threshold value. Also, the comparer 120 classifies the ECG estimation signal as the noise in response to the first comparison value being less than the predetermined first threshold value, or the second comparison value being greater than the predetermined second threshold value. The ECG estimation signal classified as the noise is discarded.

Figure 2:
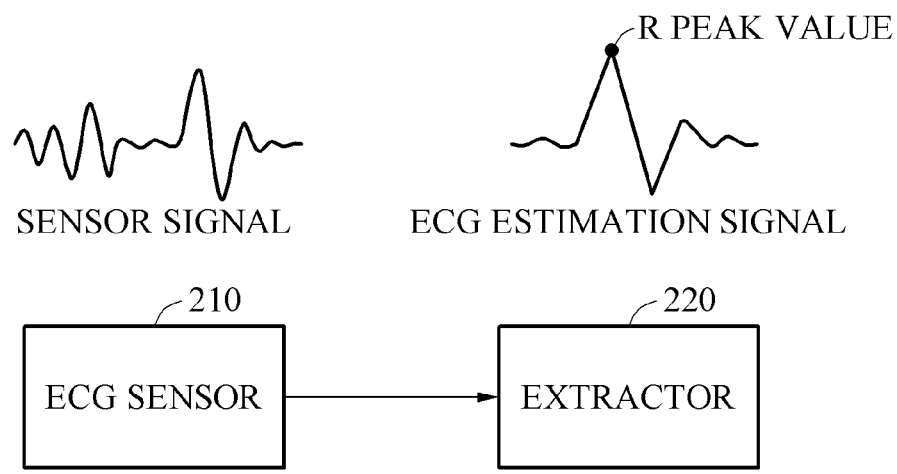
FIG. 2 is a block diagram illustrating an example of an extractor configured to extract an electrocardiography (ECG) estimation signal from a sensor signal.

FIG. 2 is a block diagram illustrating an example of an extractor 220 configured to extract an electrocardiography (ECG) estimation signal from a sensor signal. Referring to FIG. 2, an ECG sensor 210 collects a sensor signal from a user. The ECG sensor 210 collects the sensor signal, for example, through electrodes in contact with a body of the user. An electrode configured to measure an ECG signal may include a wet type electrode or a dry type electrode. The wet type electrode may measure the ECG signal more accurately than the dry type electrode, but the wet type electrode may be less convenient to use than the dry type electrode. Thus, the wet type electrode is used, for example, in a medical facility, and the dry type electrode is used, for example, in a portable device. The dry type electrode may obtain a relatively high accuracy ECG signal.

The extractor 220 receives the sensor signal from the ECG sensor 210. The extractor 220 extracts the ECG signal from the sensor signal based on a peak value of the sensor signal. For example, the extractor 220 extracts the ECG signal from the sensor signal based on an R peak value. The ECG signal extracted from the sensor signal based on the peak value of the sensor signal is referred to as an ECG estimation signal. Subsequently, the ECG estimation signal is classified as an ECG signal or a noise.

Figure 3:
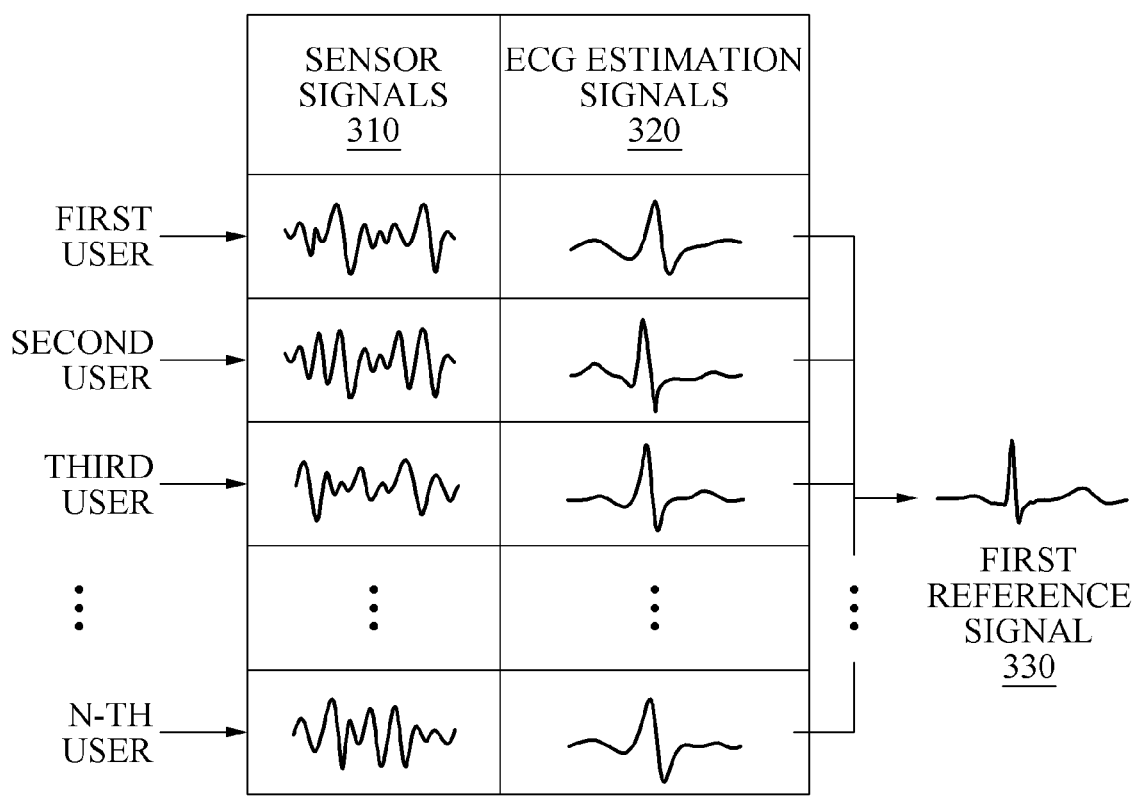
FIG. 3 illustrates an example of a method of generating a first reference signal.

FIG. 3 illustrates an example of a method of generating a first reference signal 330. Referring to FIG. 3, the first reference signal 330 is determined based on electrocardiography (ECG) estimation signals 320. Sensor signals 310 are measured, by an ECG sensor, from users including a first user and second through N-th users, where N is an integer value. The sensor signals 310 are measured during a predetermined or desired time. Hereinafter, a case in which the sensor signals 310 are extracted from multiple users is described, but the sensor signals 310 may be extracted from a single user. The ECG estimation signals 320 are extracted, by an extractor, from the respective sensor signals 310 based on peak values of the sensor signals 310. The ECG estimation signals 320 are extracted during intervals of the sensor signals 310. Based on an amount of time for measuring the sensor signals 310, a number of intervals during which the ECG estimation signals 320 are extracted from the sensor signals 310 may be increased.

Figure 6:
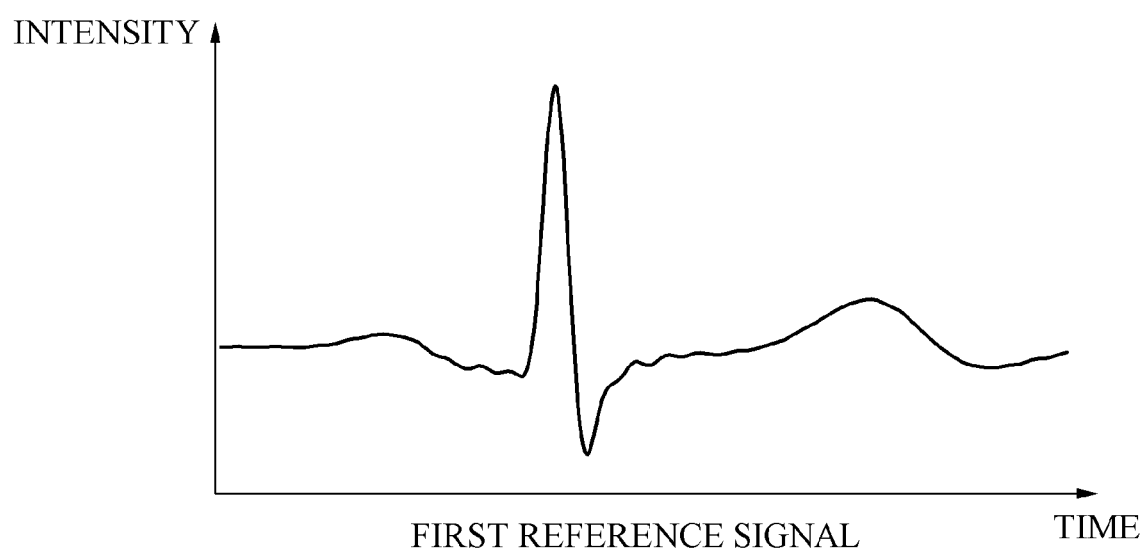
FIG. 6 is a graph illustrating an example of a first reference signal.

The first reference signal 330 is generated based on an average of the ECG estimation signals 320. Various averaging schemes may be used to calculate the average of the ECG estimation signals 320. The generated first reference signal 330 indicates an average form of ECG signals, and the generated first reference signal 330 is used to remove a noise from a signal measured from the ECG sensor. For example, as similarity between the first reference signal 330 and each of the sensor signals 310 increases, a probability that each of the sensor signals 310 is the ECG signal increases. Alternatively, as the similarity between the first reference signal 330 and each of the sensor signals 310 decreases, a probability that each of the sensor signals 310 is a noise other than the ECG signal increases. FIG. 6 is a graph illustrating an example of a first reference signal. For example, signals are measured from five hundred users for five minutes and ECG estimation signals are extracted from the respective sensor signals, and then the first reference signal depicted in FIG. 6 is determined based on an ensemble average of the ECG estimation signals.

Whether a signal measured by the ECG sensor is an ECG signal is determined based on a predetermined or desired threshold value. As the threshold value increases, a probability of removing a noise from the signal measured by the ECG sensor increases, but an individual characteristic of the ECG signal may also be removed making it more difficult to classify users based on the ECG signal. Conversely, as the threshold value decreases, the individual characteristic of the ECG signal is maintained, making it easier to classify the users based on the ECG signal, but the probability of removing the noise decreases. As such, it is of significant importance to experimentally determine an appropriate threshold value to remove the noise and classify the users.

Figure 4:
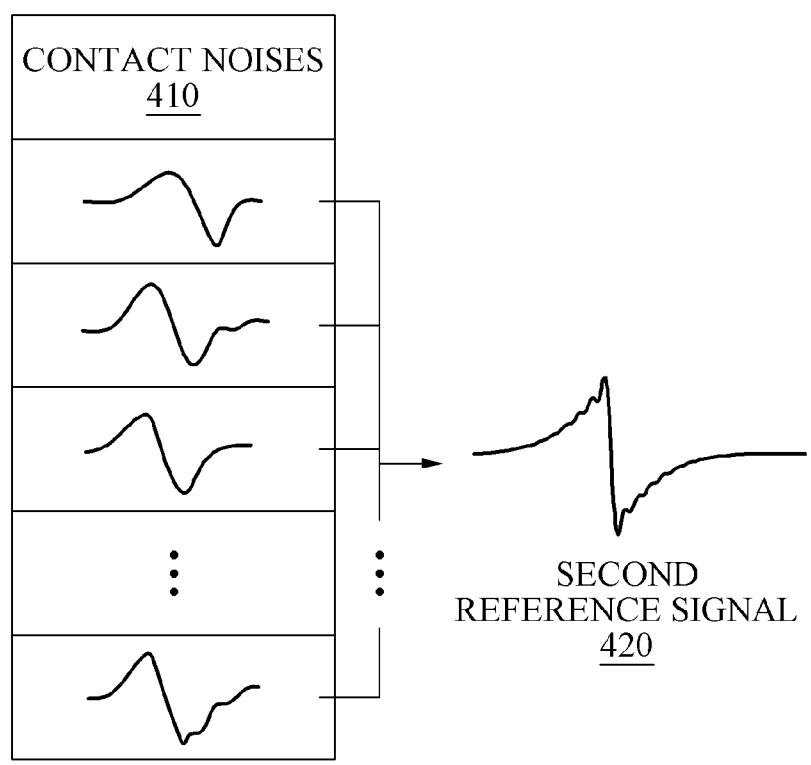
FIG. 4 illustrates an example of a method of generating a second reference signal.
Figure 7:
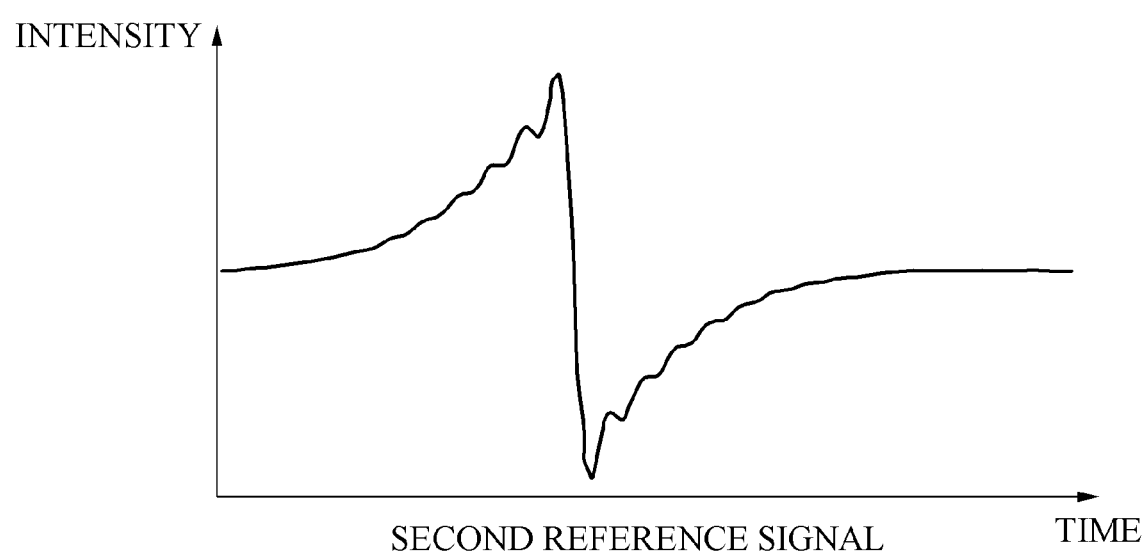
FIG. 7 is a graph illustrating an example of a second reference signal.

FIG. 4 illustrates an example of a method of generating a second reference signal 420. Referring to FIG. 4, the second reference signal 420 is generated based on an average of contact noises 410. Various averaging schemes may be used to calculate the average of the contact noises 410. The generated second reference signal 420 indicates an average form of the contact noises 410, and is used to remove a noise from a signal measured by an electrocardiography (ECG) sensor. For example, a signal similar to the second reference signal 420 may have a high probability of being a contact noise. Alternatively, a signal dissimilar to the second reference signal 420 may have a low probability of being the contact noise. Thus, an ECG estimation signal of which similarity between the ECG estimation signal and the second reference signal 420 is greater than or equal to a predetermined or desired reference value is considered to be the contact noise and thereby, the ECG estimation signal is removed. FIG. 7 is a graph illustrating an example of a second reference signal. Referring to FIG. 7, a contact noise has a form similar to a form of an ECG signal.

Whether a signal measured by the ECG sensor is a noise may be determined based on a predetermined or desired threshold value. As the threshold value decreases, a probability of removing the noise from the signal measured by the ECG sensor increases, but a probability of removing an ECG signal other than the noise also increases. Conversely, as the threshold value increases, the probability of removing the ECG signal other than the noise decreases, but the probability of removing the noise from the signal measured by the ECG sensor also decreases. As such, it is of significant importance to experimentally determine an appropriate threshold value to remove the noise from the signal measured by the ECG sensor.

Figure 5:
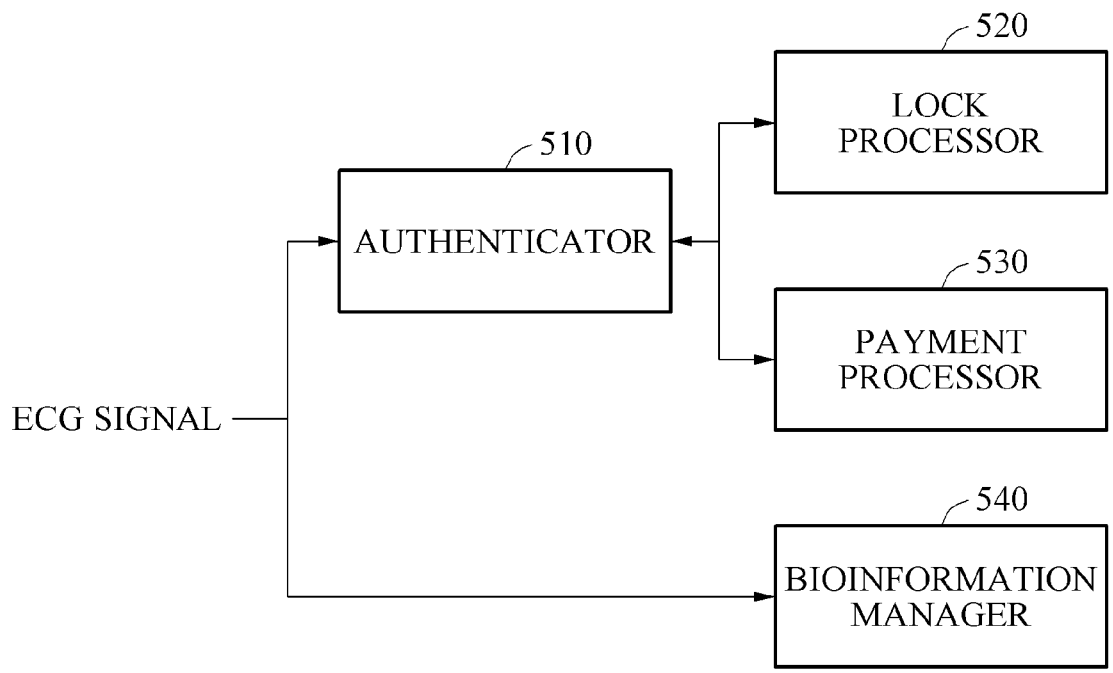
FIG. 5 illustrates an example of a linkage operation using an electrocardiography (ECG) signal.

FIG. 5 illustrates an example of a linkage operation using an electrocardiography (ECG) signal. Referring to FIG. 5, an ECG signal is used for user authentication or user health management. For example, the ECG signal is used to unlock a portable device or to make a payment through an electronic commerce system. Also, the ECG signal may be used to diagnose arrhythmia or a heart disease of a user.

A user makes a request to unlock the portable device by placing a body part in contact with an ECG sensor. The ECG signal is obtained by the aforementioned process. The ECG signal is transmitted to an authenticator 510. A lock processor 520 requests an ECG signal from the authenticator 510 for unlocking the portable device and the authenticator 510 provides the ECG signal to the lock processor 520 in response to the request. The lock processor 520 unlocks the portable device by comparing the ECG signal received from the authenticator 510 to pre-stored ECG information of the user.

In another example, the user requests that a payment be made using credit card information stored in the portable device or using a payment system of an online shopping mall by placing a body part in contact with the ECG sensor. For the payment request, a payment processor 530 requests an ECG signal from the authenticator 510, and the authenticator 510 provides the ECG signal to the payment processor 530 in response to the request. The payment processor 530 authenticates the user based on the ECG signal received from the authenticator 510, and then provides payment information pre-stored in the online shopping mall or activates the credit card based on the credit card information stored in the portable device.

The ECG signal obtained by the aforementioned processes is provided to a bioinformation manager 540. The bioinformation manager 540 accurately measures a health condition of the user based on the ECG signal. The bioinformation manager 540 checks whether the ECG signal of the user is changed by continuously accumulating the ECG signals. The bioinformation manager 540 checks a body condition of the user by comparing the ECG signal to a predetermined or desired reference value.

As accuracy of the ECG signal used for user authentication increases, reliability of the user authentication based on the ECG signal increases and thus, a speed of the user authentication increases. As the accuracy of the ECG signal used to measure the health condition of the user increases, the health condition of the user is more accurately measured.

Figure 8:
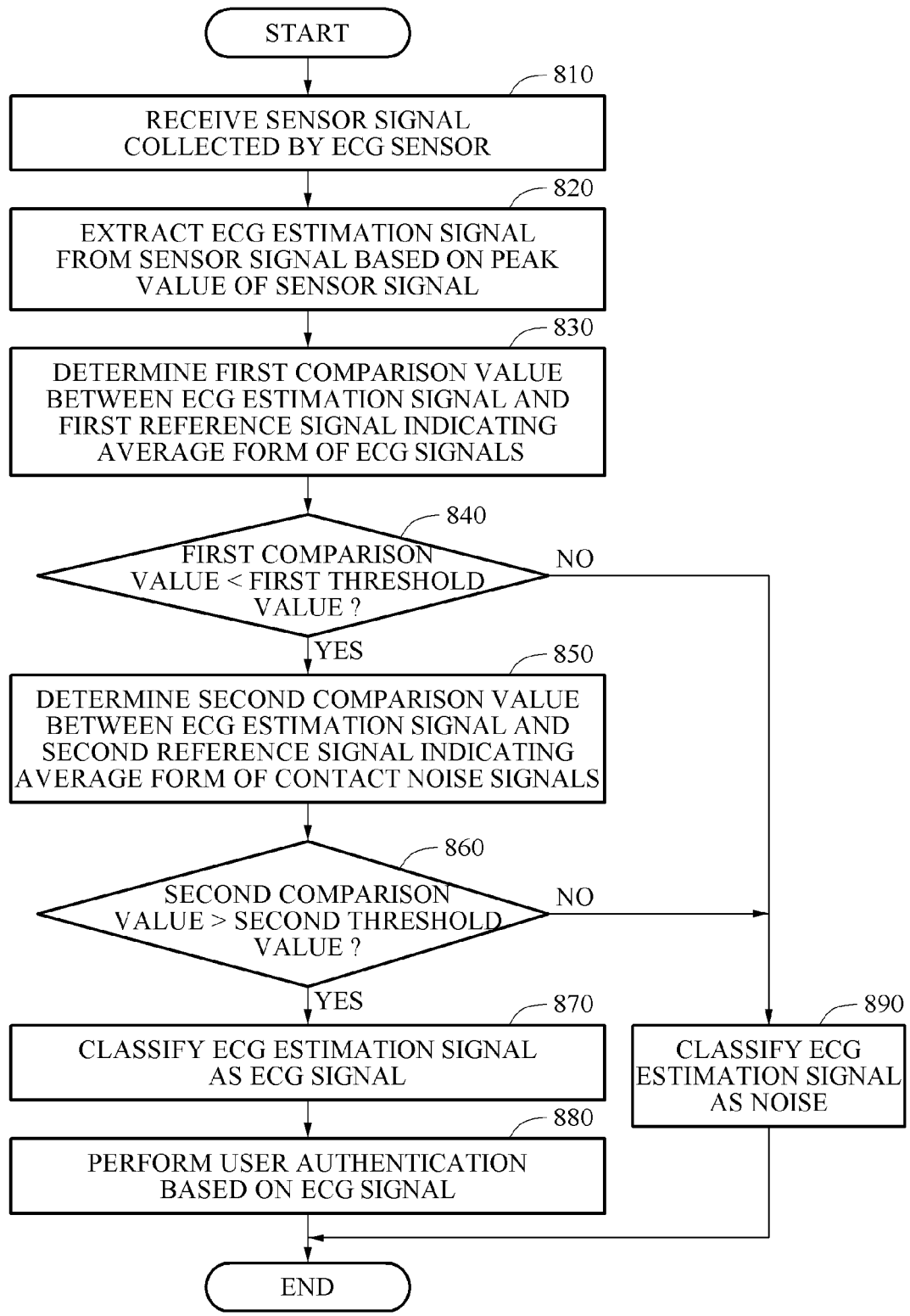
FIG. 8 is a flowchart illustrating an example process of performing user authentication based on a sensor signal.

FIG. 8 is a flowchart illustrating an example method of performing user authentication based on a sensor signal. Referring to FIG. 8, in operation 810, a noise removing apparatus receives a sensor signal collected by an electrocardiography (ECG) sensor. In operation 820, the noise removing apparatus extracts an ECG estimation signal from the sensor signal based on a peak value of the sensor signal. In operation 830, the noise removing apparatus determines a first comparison value between the ECG estimation signal and a first reference signal indicating an average form of ECG signals. In an example, the first comparison value is determined based on a cosine distance between the ECG estimation signal and a first reference signal. In operation 840, the noise removing apparatus compares the first comparison value to a first threshold value. In an example in which the first comparison value is determined based on the cosine distance between the ECG estimation signal and the first reference signal, the first threshold value is determined to be 0.357. Each of the first threshold value and the first comparison value corresponding to the cosine distance between the ECG estimation signal and the first reference signal may have a value between zero and one. In a case in which first threshold value is determined to be a value greater than an appropriate value, a probability of removing a noise from the sensor signal increases, but an individual characteristic of the ECG signal may also be removed, thereby making it more difficult to classify users based on the ECG signal. Conversely, in a case in which the first threshold value is determined to be a value lower than the appropriate value, the individual characteristic of the ECG signal may be maintained, making it easier to classify the users based on the ECG signal, but the probability of removing the noise from the sensor signal decreases. The first threshold value of 0.357 is an optimal value has been experimentally determined to maintain the individual characteristic of the ECG signal while enabling highly reliable selection of the ECG signal from the sensor signal. The noise removing apparatus performs operation 850 in response to the first comparison value being less than the first threshold value, or performs operation 890 in response to the first comparison value being greater than the first threshold value.

In operation 850, the noise removing apparatus determines a second comparison value between the ECG estimation signal and a second reference signal indicating an average form of contact noise signals. In an example, similar to the determination of the first comparison value, the second comparison value is determined based on a cosine distance between the ECG estimation signal and the second reference signal. Following operation 850, in operation 860, the noise removing apparatus compares the second comparison value to a second threshold value. In an example in which the second comparison value is determined based on the cosine distance between the ECG estimation signal and the second reference signal, the second threshold value may be 0.9. Each of the second threshold value and the second comparison value may have the value between zero and one. Then, the noise removing apparatus performs operation 870 in response to the second comparison value being greater than the second threshold value, or performs operation 890 in response to the second comparison value being less than the second threshold value.

In operation 870, the noise removing apparatus classifies the ECG estimation signal as the ECG signal. Thereafter, in operation 880, the noise removing apparatus performs user authentication based on the ECG signal.

In operation 890, the noise removing apparatus classifies the ECG estimation signal as a noise.

Figure 9:
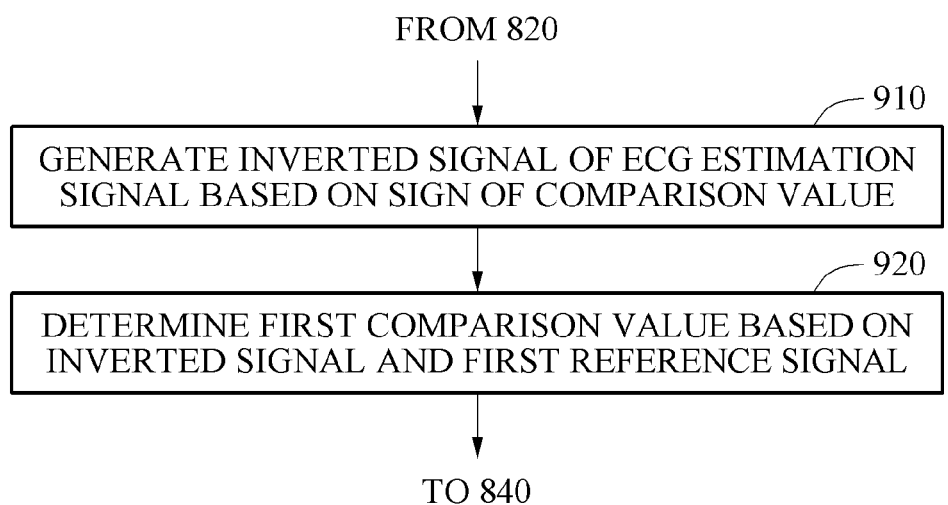
FIG. 9 is a flowchart illustrating an example process of generating an inverted signal of an electrocardiography (ECG) estimation signal.

FIG. 9 is a flowchart illustrating an example method of generating an inverted signal of an electrocardiography (ECG) estimation signal. Referring to FIG. 9, in operation 910, a noise removing apparatus generates an inverted signal of an ECG estimation signal based on a sign of a comparison value. Operation 910 is performed after operation 820 (FIG. 8) is performed. In operation 920, the noise removing apparatus determines a first comparison value based on the inverted signal and a first reference signal. The noise removing apparatus determines, as the first comparison value, a comparison value between the inverted signal and the first reference signal. Operation 840 (FIG. 8) is performed after operation 920 is performed.

A waveform of the ECG estimation signal may be inverted based on the body part placed in contact with the ECG sensor. In an example, a first reference signal is determined under an assumption that a left hand is in contact with a first electrode of the ECG sensor and a right hand is in contact with a second electrode of the ECG sensor. In this example, the ECG estimation signal having an inverted form of the first reference signal is obtained in response to the right hand being in contact with the first electrode and the left hand being in contact with the second electrode. However, the user may find it inconvenient to position the left hand and right hand at the predetermined or desired areas. The ECG signal may be obtained in response to the obtained ECG estimation signal being inverted regardless of where a hand is positioned. The noise removing apparatus obtains the ECG signal regardless of hand position by inverting the ECG estimation signal in response to the comparison value being a negative value.

Figure 10:
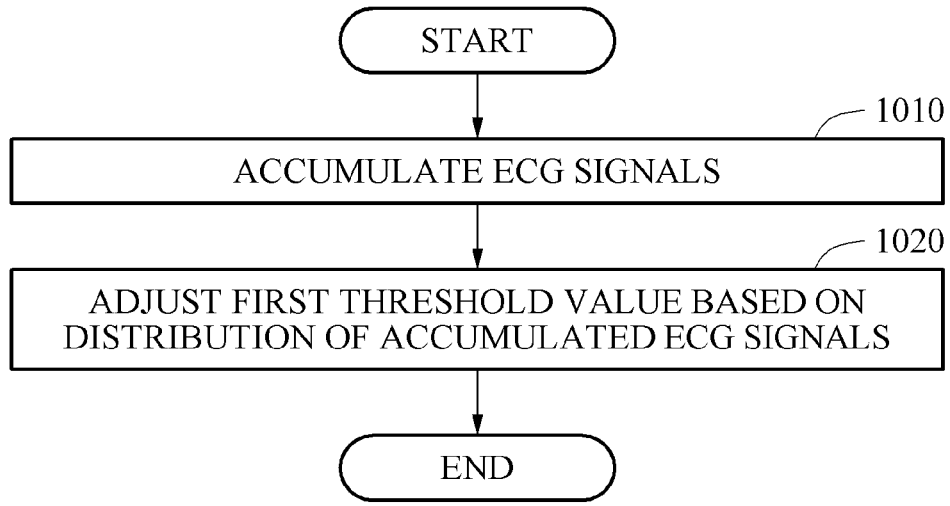
FIG. 10 is a flowchart illustrating an example process of adjusting a first threshold value.

FIG. 10 is a flowchart illustrating an example method of adjusting a first threshold value. Referring to FIG. 10, in operation 1010, a noise removing apparatus accumulates electrocardiography (ECG) signals. In operation 1020, the noise removing apparatus adjusts a first threshold value based on a distribution of the accumulated ECG signals. A small amount of accumulated ECG signal distribution may indicate that a measurement environment of a sensor signal is stable and the sensor signal is highly reliable, in which case the noise removing apparatus tightly adjusts the first threshold value. For example, the noise removing apparatus increases the first threshold value in response to the amount of accumulated ECG signal distribution being less than a preset reference.

Conversely, a great amount of accumulated ECG signal distribution may indicate that the measurement environment of the sensor signal is unstable and the sensor signal is unreliable, in which case the noise removing apparatus loosely adjusts the first threshold value. For example, the noise removing apparatus decreases the first threshold value in response to the amount of accumulated ECG signal distribution being greater than the preset reference. The noise removing apparatus also adjusts a second threshold value by a similar method.

Figure 11:
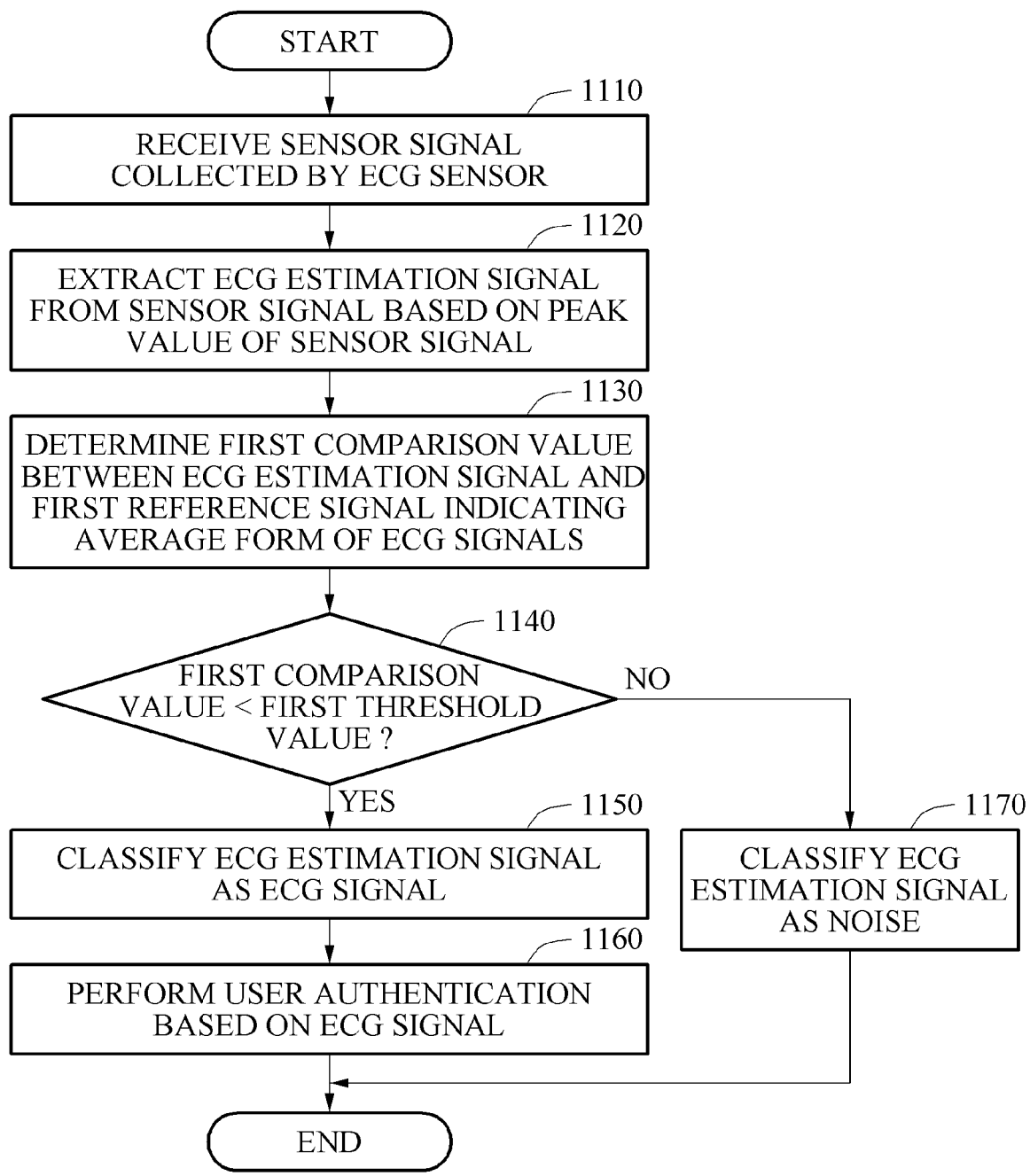
FIG. 11 is a flowchart illustrating another example process of performing user authentication based on a sensor signal.

FIG. 11 is a flowchart illustrating another example method of performing user authentication based on a sensor signal. Referring to FIG. 11, in operation 1110, a noise removing apparatus receives a sensor signal collected by an electrocardiography (ECG) sensor. In operation 1120, the noise removing apparatus extracts an ECG estimation signal from the sensor signal based on a peak value of the sensor signal. In operation 1130, the noise removing apparatus determines a first comparison value between the ECG estimation signal and a first reference signal indicating an average form of ECG signals. In an example, the first comparison value is determined based on a Euclidean distance between the ECG estimation signal and the first reference signal. The calculation may be less complex when a Euclidean distance is used than when a cosine distance is used as a comparison value. When the Euclidean distance is used as the comparison value, an intensity of a noise of the sensor signal is greater than an intensity of an ECG signal and thus, the ECG estimation signal may not be compared to waveforms of contact noises. Also, when the Euclidean distance is used as the comparison value, the comparison value may be determined based on a resolution power and a range of an analog-to-digital (ADC) converter of a system to which the noise removing apparatus is applied. In operation 1140, the noise removing apparatus compares the first comparison value to a first threshold value. The noise removing apparatus performs operation 1150 in response to the first comparison value being less than the first threshold value. Alternatively, the noise removing apparatus performs operation 1170 in response to the first comparison value being greater than the first threshold value.

In operation 1150, the noise removing apparatus classifies the ECG estimation signal as the ECG signal. Thereafter, in operation 1160, the noise removing apparatus performs user authentication based on the ECG signal.

In operation 1170, the noise removing apparatus classifies the ECG estimation signal as a noise.

Figure 12:
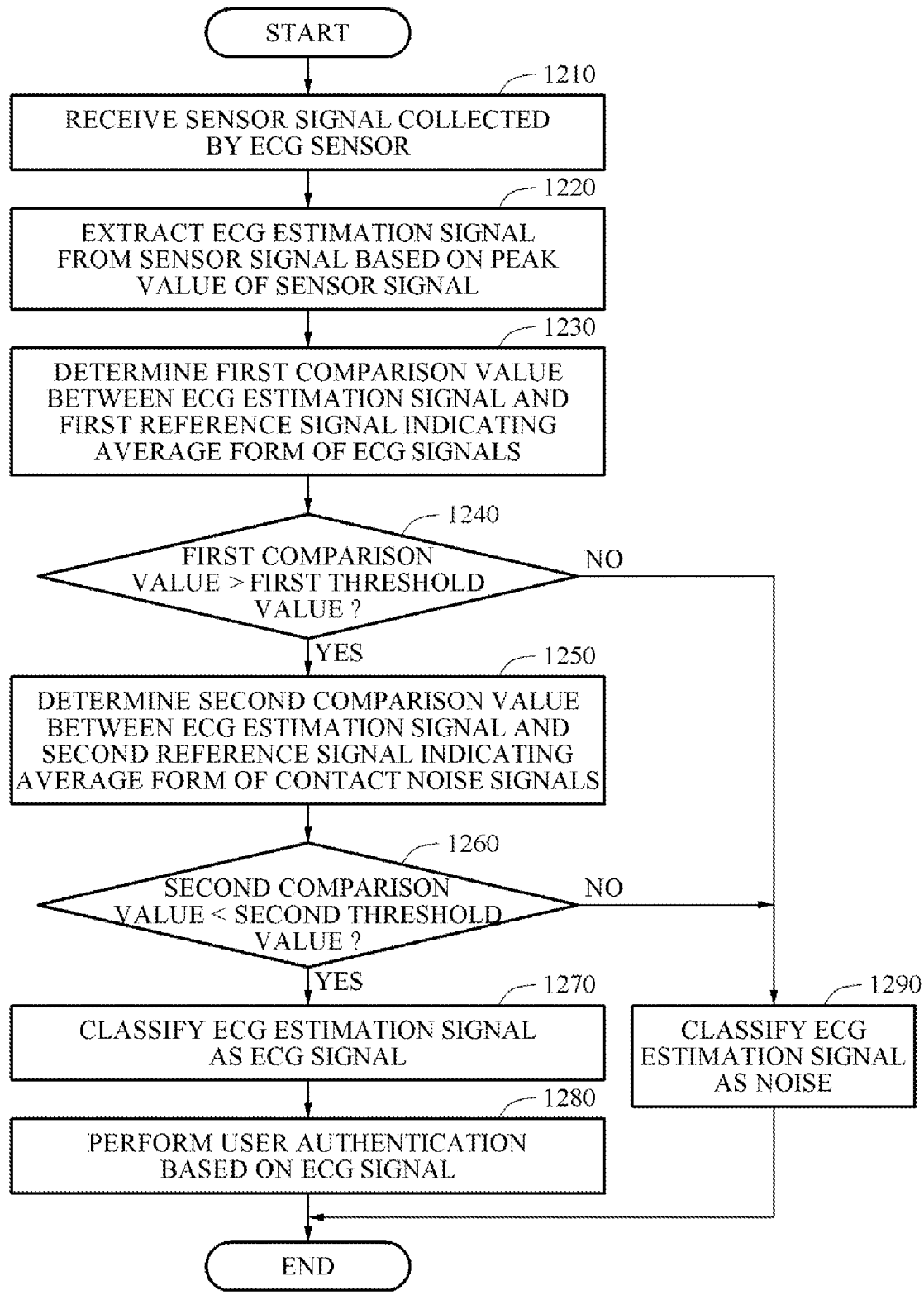
FIG. 12 is a flowchart illustrating another example process of performing user authentication based on a sensor signal.

FIG. 12 is a flowchart illustrating another example method of performing user authentication based on a sensor signal. Referring to FIG. 12, in operation 1210, a noise removing apparatus receives a sensor signal collected by an electrocardiography (ECG) sensor. In operation 1220, the noise removing apparatus extracts an ECG estimation signal from the sensor signal based on a peak value of the sensor signal. In operation 1230, the noise removing apparatus determines a first comparison value between the ECG estimation signal and a first reference signal indicating an average form of ECG signals. In an example, the first comparison value is determined based on a correlation between the ECG estimation signal and the first reference signal. In operation 1240, the noise removing apparatus compares the first comparison value to a first threshold value. The first comparison value may be experimentally determined to remove a motion noise from the sensor signal. The motion noise is a noise having a different form than an ECG signal while maintaining an individual characteristic of the ECG signal. The noise removing apparatus performs operation 1250 in response to the first comparison value being greater than the first threshold value. Alternatively, the noise removing apparatus performs operation 1290 in response to the first comparison value being less than the first threshold value.

In operation 1250, the noise removing apparatus determines a second comparison value between the ECG estimation signal and a second reference signal indicating an average form of contact noise signals. In an example, similar to the determination of the first comparison value, the second comparison value is determined based on a correlation between the ECG estimation signal and the second reference signal. Thereafter, in operation 1260, the noise removing apparatus compares the second comparison value to a second threshold value. As with the first comparison value, the second comparison value may also be experimentally determined. The noise removing apparatus performs operation 1270 in response to the second comparison value being less than the second threshold value. Alternatively, the noise removing apparatus performs operation 1290 in response to the second comparison value being greater than the second threshold value.

In operation 1270, the noise removing apparatus classifies the ECG estimation signal as the ECG signal. Thereafter, in operation 1280, the noise removing apparatus performs user authentication based on the ECG signal.

In operation 1290, the noise removing apparatus classifies the ECG estimation signal as a noise.

Figure 13:
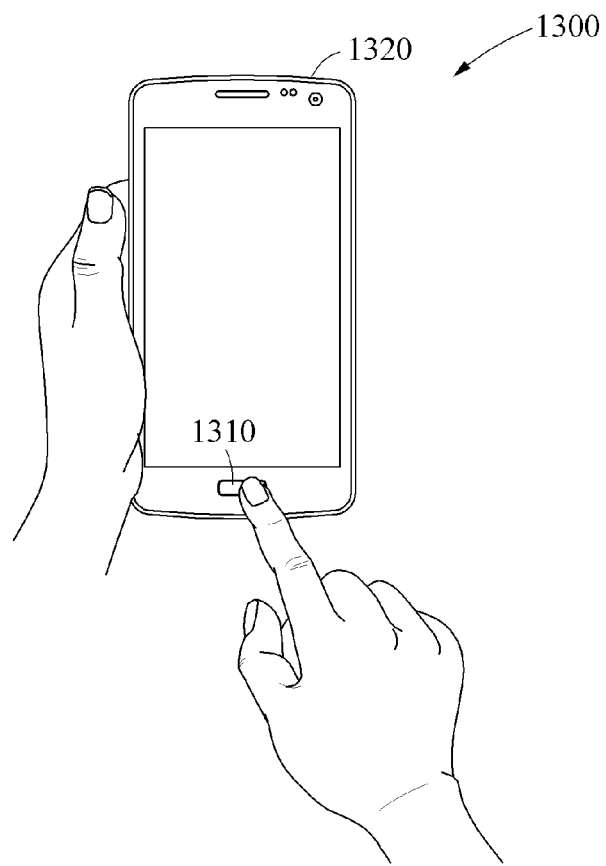
FIG. 13 is a diagram illustrating a type of a smartphone configured to obtain an electrocardiography (ECG) signal.

FIG. 13 is a diagram illustrating a type of a smartphone 1300 that may obtain an electrocardiography (ECG) signal. Referring to FIG. 13, the smartphone 1300 includes a home button 1310 and a bezel 1320. The home button 1310 and the bezel 1320 each include an electrode. The electrodes of the home button and the bezel may be dry type electrodes. The smartphone 1300 collects a sensor signal from a body part of a user placed in contact with the smartphone 1300. The smartphone 1300 collects the sensor signal from one hand of the user in contact with the electrode of the home button 1310 and an opposite hand of the user in contact with the electrode of the bezel 1320. For example, the smartphone collects the sensor signal from a palm of the one hand in contact with the bezel 1320 and a finger of the opposite hand in contact with the home button 1310. The smartphone obtains an ECG signal from the sensor signal by the aforementioned processes.

Figure 14:
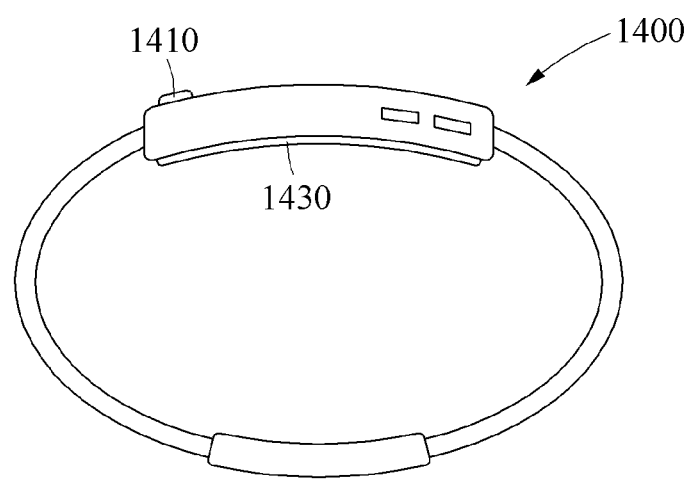
FIG. 14 is a diagram illustrating a type of a smartwatch configured to obtain an electrocardiography (ECG) signal.

FIG. 14 is a diagram illustrating a type of a smartwatch 1400 that may obtain an electrocardiography (ECG) signal. Referring to FIG. 14, the smartwatch 1400 includes a home button 1410 and a backside electrode 1430. The home button 1410 includes an electrode. The home button electrode and the backside electrode 1430 may be dry type electrodes. The smartwatch 1400 collects a sensor signal from a body part of a user in contact with the smartwatch 1400. For example, the smartwatch 1400 collects the sensor signal from a wrist of the user in contact with the backside electrode 1430 and a finger of the user in contact with the home button 1410. The smartwatch 1400 obtains an ECG signal from the sensor signal based on the aforementioned processes.

Figure 15:
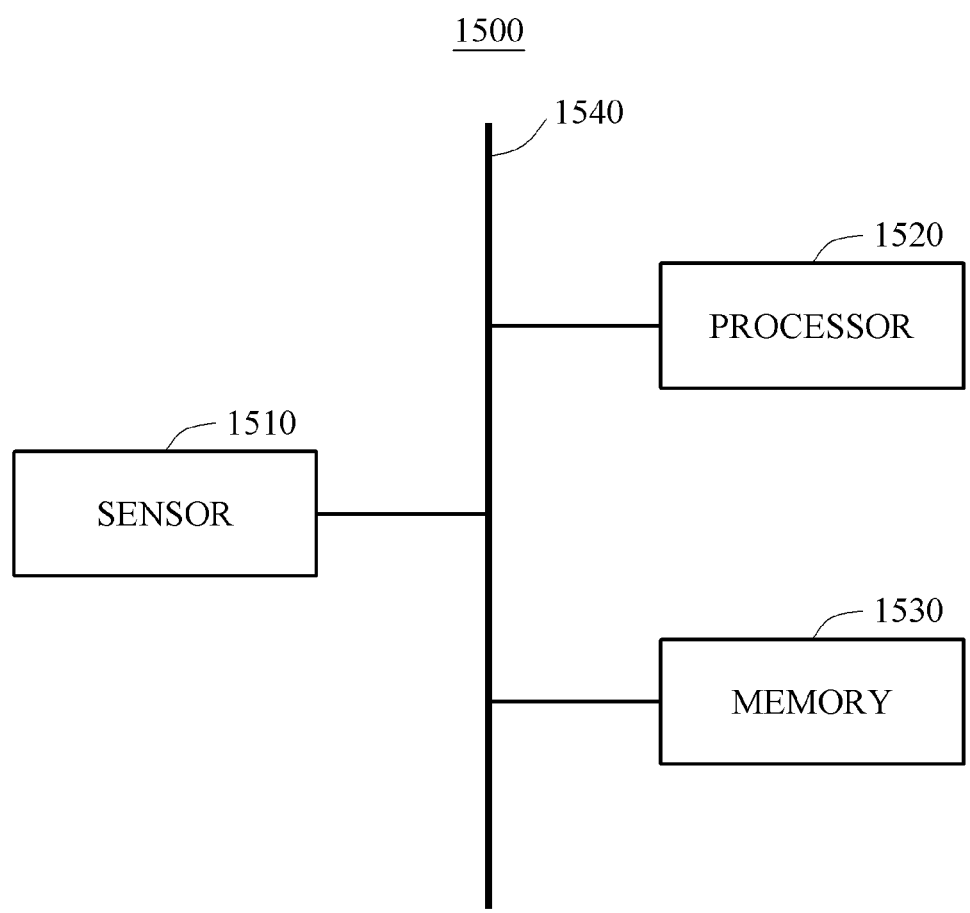
FIG. 15 is a diagram illustrating an example of an electronic device.

FIG. 15 is a diagram illustrating an example of an electronic device 1500. Referring to FIG. 15, an electronic device 1500 includes a sensor 1510, a processor 1520, and a memory 1530. The sensor 1510, the processor 1520, and the memory 1530 communicate with each other through a bus 1540. The electronic device 1500 may be a portable device, for example, a smartphone, a tablet personal computer (PC), or a notebook, or a wearable device, for example, a smartwatch, a smartband, or an item of smartwear.

The sensor 1510 collects a sensor signal from a user. For example, the sensor 1510 outputs the sensor signal with respect to an ECG signal of the user. The processor 1520 may include one or more of the modules described with reference to FIGS. 1 through 14, or may perform one or more of the methods described with reference to FIGS. 1 through 14. The processor 1520 executes an application and controls the electronic device 1500. Commands used to execute applications are stored in the memory 1530. The electronic device 1500 is connected to an external device, for example, a PC or a network, through an input and output device (not shown), to thereby perform a data exchange.

The extractor 110 and comparer 120 in FIG. 1, the ECG sensor 210 and the extractor 220 in FIG. 2, the authenticator 510, the lock processor 520, the payment processor 530 and the bioinformation manager 540 in FIG. 5, and the sensor 1510, the processor 1520 and the memory 1530 in FIG. 15 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3, 4 and 8-12 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A noise removing method comprising:
   receiving a sensor signal collected by an electrocardiography (ECG) sensor;
   extracting an ECG estimation signal from the sensor signal based on a peak value of the sensor signal;
   determining a first comparison value by comparing the ECG estimation signal and a first reference signal indicating an average form of reference ECG signals, the first reference signal being generated by combining and averaging the reference ECG signals;
   determining a second comparison value by comparing the ECG estimation signal and a second reference signal indicating an average form of contact noise signals, the second reference signal being generated by combining and averaging the contact noise signals;
   classifying the ECG estimation signal as one of an ECG signal and a noise signal based on a first comparison result between the first comparison value and a first threshold value and a second comparison result between the second comparison value and a second threshold value;
   accumulating ECG signals based on the ECG signal in response to the ECG estimation signal being classified as the ECG signal;
   accumulating noise signals based on the noise signal in response to the ECG estimation signal being classified as the noise signal; and
   adjusting the first threshold value and the second threshold value based on a distribution of the accumulated ECG signals and the accumulated noise signals, wherein
   the adjusting of the first threshold value and the second threshold value includes:
   increasing the first threshold value and the second threshold value in response to the distribution of the accumulated ECG signals and the accumulated noise signals being less than a preset reference; and
   decreasing the first threshold value and the second threshold value in response to the distribution of the accumulated ECG signals and the accumulated noise signals being greater than the preset reference.

2. The method of claim 1, wherein the first reference signal is generated based on an average of the reference ECG signals collected from at least one user.

3. The method of claim 1, wherein:
   the first comparison value and the second comparison value are determined based on one of a cosine distance and a Euclidean distance; and
   the classifying comprises classifying the ECG estimation signal as the ECG signal, in response to the first comparison value being less than a first threshold value and the second comparison value being greater than a second threshold value.

4. The method of claim 3, wherein each of the first threshold value and the first comparison value corresponding to the cosine distance between the ECG estimation signal and the first reference signal has a value between 0 and 1.

5. The method of claim 1, wherein the first comparison value is determined based on one of a cosine distance between the ECG estimation signal and the first reference signal, a correlation between the ECG estimation signal and the first reference signal, and a Euclidean distance between the ECG estimation signal and the first reference signal.

6. The method of claim 1, wherein a first threshold value for comparison with the first comparison value is experimentally determined to remove the noise signal and classify users based on the ECG signal.

7. The method of claim 1, further comprising:
performing user authentication based on the ECG signal.

8. The method of claim 1, wherein the ECG sensor is configured to collect the sensor signal through a dry type electrode.

9. The method of claim 1, wherein the ECG sensor comprises:
a first electrode disposed in a bezel of a portable device and configured to collect the sensor signal from a hand of the user in contact with the first electrode; and
a second electrode disposed in a home button of the portable device and configured to collect the sensor signal from another hand of the user in contact with the second electrode.

10. A non-transitory computer-readable storage medium storing instructions that, when executed by a processor, cause the processor to perform the method of claim 1.

11. The method of claim 1, wherein,
the first comparison and the second comparison value are determined based on a correlation; and
the classifying comprises classifying the ECG estimation signal as the ECG signal, in response to the first comparison value being greater than a first threshold value and the second comparison value being less than a second threshold value.

12. The method of claim 1, wherein the determining comprises:
generating an inverted signal of the ECG estimation signal based on a sign of the first comparison value; and
determining a comparison value between the inverted signal and the first reference signal as the first comparison value.

13. The method of claim 1, further comprising:
removing the noise signal; and
classifying users based on the ECG signal.

14. A noise removing method comprising:
receiving a sensor signal collected by an electrocardiography (ECG) sensor;
extracting an ECG estimation signal from the sensor signal based on a peak value of the sensor signal;
determining a first comparison value by comparing the ECG estimation signal and a first reference signal indicating an average form of reference ECG signals, the first reference signal being generated by combining and averaging the reference ECG signals;
determining a second comparison value by comparing the ECG estimation signal and a second reference signal indicating an average form of contact noise signals, the second reference signal being generated by combining and averaging the contact noise signals;
classifying the ECG estimation signal as one of an ECG signal and a noise signal based on a first comparison result between the first comparison value and a first threshold value and a second comparison result between the second comparison value and a second threshold value;
accumulating ECG signals based on the ECG signal in response to the ECG estimation signal being classified as the ECG signal;
accumulating noise signals based on the noise signal in response to the ECG estimation signal being classified as the noise signal; and
adjusting the first threshold value and the second threshold value based on a distribution of the accumulated ECG signals and the accumulated noise signals,
wherein the determining of the first comparison value further comprises:
generating an inverted signal of the ECG estimation signal based on a sign of the first comparison value; and
determining a comparison value between the inverted signal and the first reference signal as the first comparison value,
wherein the ECG estimation signal comprises a noise component such that a waveform of the ECG estimation signal is not specified through a threshold-based comparison, and
wherein the adjusting of the first threshold value and the second threshold value includes:
increasing the first threshold value and the second threshold value in response to the distribution of the accumulated ECG signals and the accumulated noise signals being less than a preset reference; and
decreasing the first threshold value and the second threshold value in response to the distribution of the accumulated ECG signals and the accumulated noise signals being greater than the preset reference.

15. A noise removing apparatus comprising:
an extractor configured to receive a sensor signal collected by an electrocardiography (ECG) sensor, and extract an ECG estimation signal from the sensor signal based on a peak value of the sensor signal; and
a comparer configured to:
determine a first comparison value by comparing the ECG estimation signal and a first reference signal indicating an average form of reference ECG signals, the first reference signal being generated by combining and averaging the reference ECG signals;
determine a second comparison value by comparing the ECG estimation signal and a second reference signal indicating an average form of contact noise signals, the second reference signal being generated by combining and averaging the contact noise signals;
classify the ECG estimation signal as one of an ECG signal and a noise signal based on a first comparison result between the first comparison value and a first threshold value and a second comparison result between the second comparison value and a second threshold value;
accumulate ECG signals based on the ECG signal in response to the ECG estimation signal being classified as the ECG signal, accumulate noise signals based on the noise signal in response to the ECG estimation signal being classified as the noise signal; and adjust the first threshold value and the second threshold value based on a distribution of the accumulated ECG signals and the accumulated noise signals, wherein the adjusting of the first threshold value and the second threshold value includes:

increasing the first threshold value and the second threshold value in response to the distribution of the accumulated ECG signals and the accumulated noise signals being less than a preset reference; and decreasing the first threshold value and the second threshold value in response to the distribution of the accumulated ECG signals and the accumulated noise signals being greater than the preset reference.

16. The apparatus of claim 15, wherein the first reference signal is generated based on an average of the reference ECG signals collected from at least one user.

17. The apparatus of claim 15, wherein:

the first comparison value and the second comparison value are determined based on a cosine distance or a Euclidean distance; and the comparer is configured to classify the ECG estimation signal as the ECG signal, in response to the first comparison value being less than a first threshold value and the second comparison value being greater than a second threshold value.

18. The apparatus of claim 15, wherein the ECG signal is used to perform user authentication.

* * * * *